(12) United States Patent
Sager et al.

(10) Patent No.: US 6,960,658 B1
(45) Date of Patent: Nov. 1, 2005

(54) MASPIN TRANSCRIPTIONAL REGULATORY SEQUENCES AND USES THEREOF

(75) Inventors: Ruth Sager, deceased, late of Brookline, MA (US); Arthur Pardee, legal representative, Brookline, MA (US); Ming Zhang, Pearland, TX (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 610 days.

(21) Appl. No.: 09/617,174

(22) Filed: Jul. 17, 2000

Related U.S. Application Data

(63) Continuation of application No. 09/155,380, filed on Sep. 28, 1998, now abandoned, which is a continuation of application No. PCT/US97/05186, filed on Mar. 28, 1997.
(60) Provisional application No. 60/014,368, filed on Mar. 28, 1996.

(51) Int. Cl.[7] .............................................. C07H 21/04
(52) U.S. Cl. .................... 536/23.4; 435/320.1; 435/325
(58) Field of Search .............................. 536/24.1, 23.1, 536/23.5; 435/320.1, 325

(56) References Cited

U.S. PATENT DOCUMENTS 5,470,970 A    11/1995  Sager et al. ................ 536/23.5

OTHER PUBLICATIONS

Verma IM, et al. Nature 1997 Sep 18; 389 (6648): 239–42.*
Memorandum, Department of Health & Human Services, "Serious Adverse Event in a Study of Gene Transfer in X-Linked severe Combined Immunodeficiency", Jan. 14, 2003.*
Pandha HS, et al. Curr Opin Invest Drugs 2000; 1 (1): 122–34.*
Amalfitano A, et al. Curr Gene Ther 2002; 2: 111–33.*
Houdebine LM. J Biotechnol May 31, 1994; 34 (3): 269–87.*
Maas N, et al. Tumor Diagnostk und Therapie 1997; 18 (4): 89–96.*
Zhang M, et al. Cell Growth and Differentiation Feb. 1997; 8 (2): 179–186.*
Zhang M, et al. Proc Natl Acad Sci USA May 27, 1997; 94 (11) 5673–5678*
Zou Z, et al. J Biol Chem Mar. 3, 2000; 275 (9): 6051–6054.*
Liotta et al., "Cancer Metastasis and Angiogenesis: An Imbalance of Positive and Negative Regulation" Cell 64(2):327–336, 1991.
Sager et al., "Maspin: A tumor Suppressing Serpin" Curr. Top. In Microbiol. And Immunol. 213(1):51–64, 1996.
Sheng et al., "Production, Purification, and Characterization of Recombinant Maspin Proteins" J. of Biol. Chem. 269(40):30988–30993, 1994.
Zou et al., "Maspin, a Serpin with Tumor-Suppressing Activity in Human Mammary Epithelial Cells" Science 263:441–580, 1994.

* cited by examiner

*Primary Examiner*—Yvonne Eyler
*Assistant Examiner*—Stephen L. Rawlings
(74) *Attorney, Agent, or Firm*—Fish & Richardson P.C.

(57) ABSTRACT

Isolated nucleic acid molecules that include transcriptional regulatory sequences of the maspin gene are described. These nucleic acid molecules are useful for identifying compounds and proteins that alter expression of maspin in mammary cells and other cell types.

11 Claims, 13 Drawing Sheets

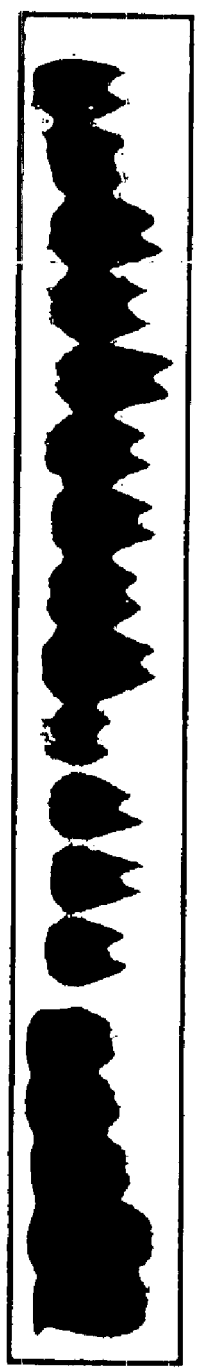 
FIG. 1

Maspin 
Maspin 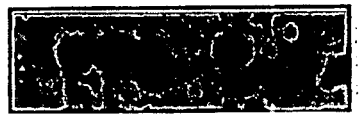
36B4 
Actin 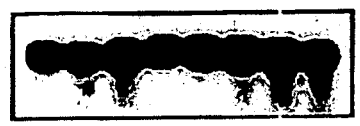
FIG. 2

```
-956  AGATAAGCACAGCAGAGAAGCAACCAGCTCCGTTTCAGGTCCTTTCCTGAGGCTGATTCG         -897

-896  GCTGGAAGGGAGTAGGTCCCACCAAATGAAGAAGCTGTGGGAAGACAGGAGGACAAGAAC        -837

-836  AGGCTCCACGAAGAGATTTCAGAGCAGAGCTGCGTACTCCTTTTTCTTTTTGTTTCTTTT         -777

-776  GCTCTGTCACCCAGGCTGAAGTACAGTGGTTAGCTCACGGCTCACTGCAGCTTTGACCTC         -717

-716  CCAGGCTCAAGTGATCCTCTCGTCTCAGCTTTCCAAGTAACTGGGACCACAGGCATGCAT         -657

-656  CACCACGCTAGGCTATTGTTTTACATTTTTTGTAGAGATGGGGTCTCACCATGTTGCCCA         -597

-596  GGTTGGTCTCAAACTCCTGGGCTCAAGCAATCCGCTCACGTCAACCTCCCCAAATGCTGG        -537
                                          AP2        AP1
-536  GATTACAGGCGTGAGCCACCG GCCAGGC TGAGTAA TCCTAATCACAGGATTTTAAAAA       -477
              Ets
-476  GAAA CTTCCT GCGCCACCCATTAAACAATATCTCCTACCAATTTGGTAGTAAATATTTTG     -417

-416  CTAATAGTACCTAATTTTTAGGTAGGCACTGTGTTTATACATATATCCATTCCTTCTTTT        -357

-356  TTGATTGTCTTTCTGTTTAATGGGCAGCTACCTCTCTTGGCATCTAGCAGAATGAGCTGC        -297
                                 GRE
-296  TGCAGTTTACACAAAAAGAATGG AGATCAGA GTACTTTTTGTGCCACCAACGTGTCTGAG     -237

-236  AAATTTGTAGTGTTACTATCATCACACATTACTTTTATTTCATCGAATATTTCACCTTCC        -177

-176  GGTCCTGCGTGGGCCGAGAGGATTGCCGTACGCATGTCTGTACGTATGCATGTAACTCAC        -117
             Ets
-116  AGCCC CTTCCT GCCCGAACATGTTGGAGGCCTTTTGGAAGCTGTGCAGACAACAGCAACT      -57
          AP1
-56   TCAGCC TGAATCA TCTCTTTCAATTGTGGACAAGCTGCCAAGAGGCTTGAGTAGGAG

1     AGGAGTGCCGCCGAGGCGGGGCGGGGCGGGGCGTGGAGCTGGGCTGGCAGTGGGCGTGGC         60

61    GGTGCTGCCCAGGTGAGCCACCGCTGCTTCTGCCCAGACACGGTCGCCTCCACATCCAGG        120

121   TCTTTGTGCTCCTCGCTTGCCTGTTCCTTTTCCACGCATTTTCCAGGATAACTGTGACTC        180

181   CAGG
```

FIG. 3

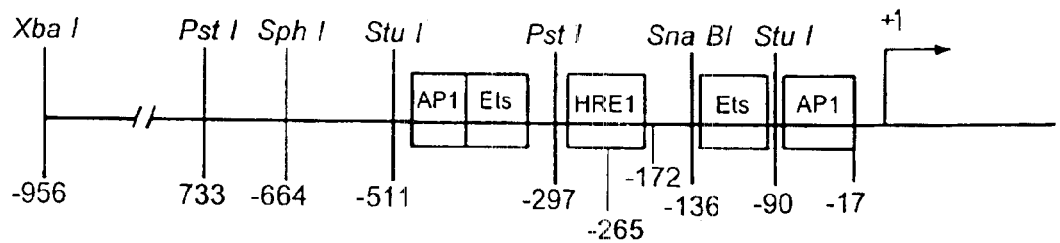
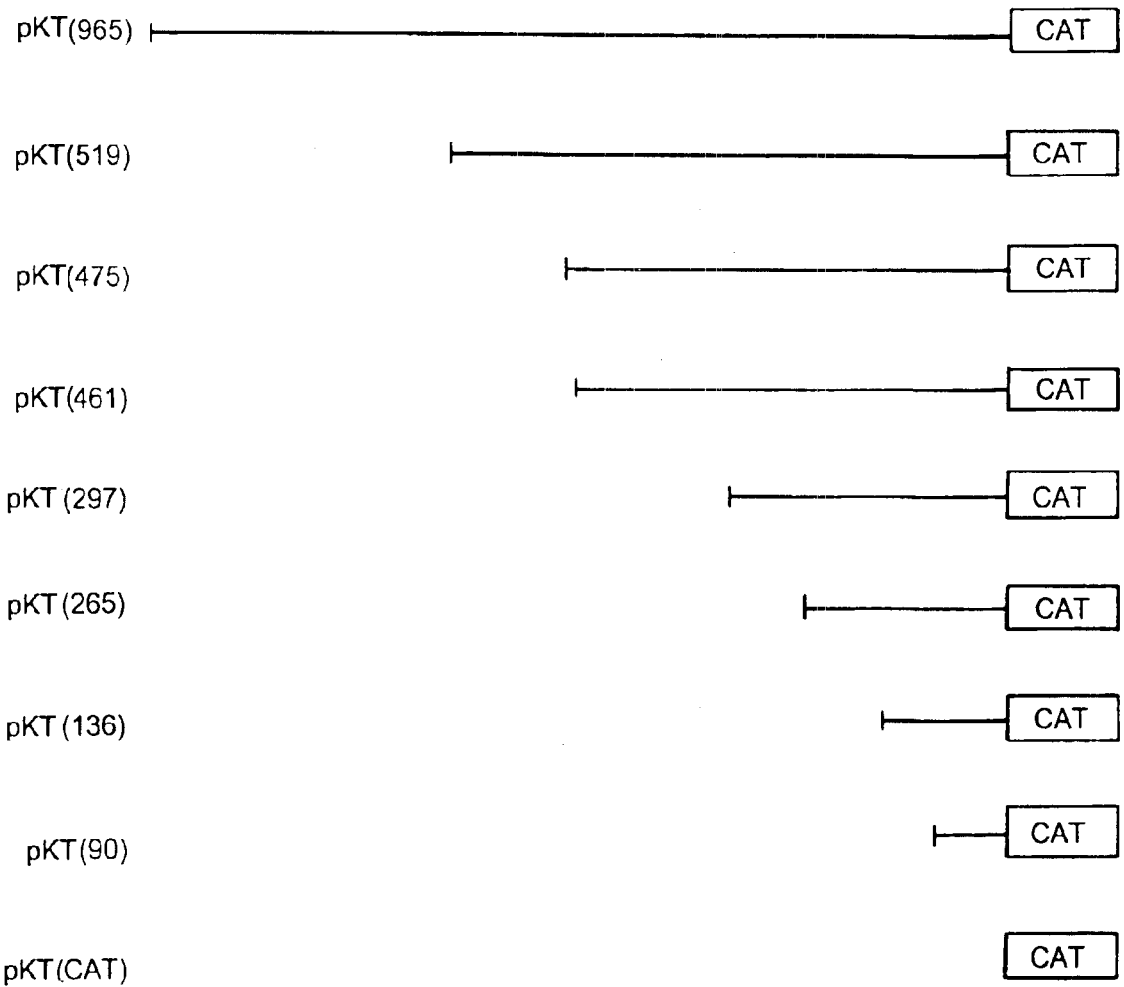
FIG. 9A

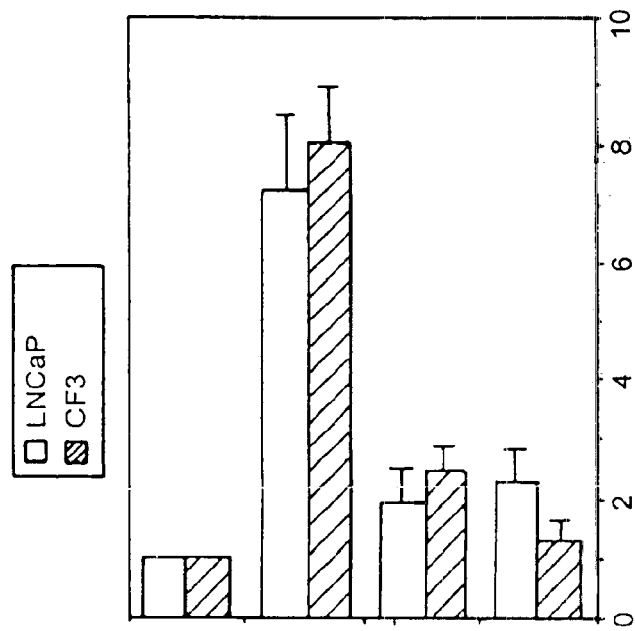
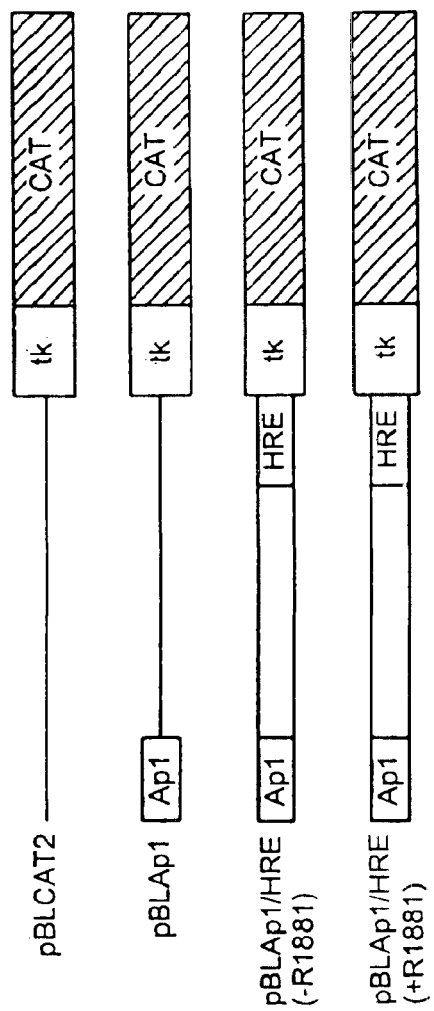
FIG. 12B
FIG. 12A

MASPIN TRANSCRIPTIONAL REGULATORY SEQUENCES AND USES THEREOF

RELATED APPLICATION INFORMATION

This application is a continuation of U.S. Ser. No. 09/155,380, filed Sep. 28, 1998, which is now abandoned and is a continuation of PCT Application US97/05186, filed Mar. 28, 1997, which claims priority from U.S. Ser. No. 60/014,368, filed Mar. 28, 1996.

STATEMENT AS TO FEDERALLY SPONSORED RESEARCH

The work described herein was supported in part by National Institutes of Health Grant CA 61253. The United States Government therefore may have certain rights in the invention.

FIELD OF THE INVENTION

The invention relates to DNA sequences which regulate transcription of the maspin gene and methods for screening compounds to identify candidate compounds for treatment of breast cancer and prostate cancer.

BACKGROUND OF THE INVENTION

Proteases and protease inhibitors are known to play important roles in tumor invasion and metastasis (Liotta et al., Cell 64:327, 1991). Proteinase degradation of the extracellular matrix is a prerequisite to invasion and metastasis. Proteinase inhibitors function to prevent this process.

Maspin is a serpin expressed in normal human mammary epithelial cells (Sager et al., U.S. Pat. No. 5,470,970; Zou et al., Science 263:526, 1994). Maspin expression in these cells decreases with increasing malignancy, and its expression is lost in metastases (Zou et al., supra).

Maspin, whether expressed in tumor transfectants or added as recombinant maspin from outside tumor cells, inhibits invasion in a Boyden chamber assay (Sheng et al., J. Biol. Chem. 269:30988, 1994). In addition, maspin protein has been shown to inhibit mobility of tumor cells (Sager et al., Curr. Top. Microbiol. Immunol. 1:51, 1995).

SUMMARY OF THE INVENTION

The invention features transcriptional regulatory sequences which affect expression of the maspin gene. Maspin is described by Sager et al., U.S. Pat. No. 5,470,970, hereby incorporated by reference.

It is desirable to identify activators of maspin expression because such compounds can be used to increase expression of maspin in mammary tumor cells and certain prostate tumors. Increased expression of maspin will lead to decreased protease activity and reduced tumor spread. Accordingly, compounds which increase maspin expression can be used to inhibit growth or spread of certain mammary tumors and certain prostate tumors.

The maspin transcriptional regulatory sequences described herein (an others) can be operably linked to a reporter gene, e.g., a CAT gene or green florescent protein gene, to create reporter constructs useful in assays for compounds which affect expression of the maspin gene. This operable linkage can be accomplished by positioning the regulatory sequence 5' to sequences encoding the reporter gene so as to permit the regulatory sequences to direct expression of the reporter gene. These reporter constructs can be introduced into any suitable tumor cell line, including any of the tumor cell lines described herein. In addition, it may be desirable to introduce reporter gene constructs into normal mammary or prostate cells and measure expression in these cells. By measuring the level of reporter gene expression in tumor cells exposed to a selected compound and otherwise identical tumor cells not exposed to the selected compound, one can identify compounds which are likely to increase maspin expression. These compounds are candidate compounds for treatment of breast and prostate cancer.

In designing expression constructs it is not necessary to include the entire maspin regulatory region described herein (nucleotide −956 to nucleotide −1 of FIG. 3; nucleotides 1–957 of SEQ ID NO:1). The Ets recognition element having the sequence CTTCCT and located at nucleotides −111 to −105 (FIG. 3) is a significant sequence element, which is preferably included in the reporter construct. In various preferred embodiments the reporter construct includes this Ets element and the 10, 20, 30, 40, 50, 60, or 100 nucleotides located 3' thereof. In other preferred embodiments the construct includes this Ets element and the 10, 20, 30, 40, 50, 60, or 100 nucleotides located 5' thereof. In still other preferred embodiments the reporter construct includes this Ets element and 10, 20, 30, 40, 50, 60, or 100 nucleotides located 5' and 3' thereof. In other preferred embodiments, the construct includes the AP2, AP1, Ets, and HRE elements shown in FIG. 3. Thus, in a preferred embodiment, the construct includes the sequence from nucleotide −44 to nucleotide −514 as shown in FIG. 3.

The HRE element (also referred to as the "GRE" element), described in detail below, is an important negative regulatory element that is preferably included in expression constructs.

In general, the reporter gene should include enough of the sequence between −956 and −1 to confer a selected tumor specific pattern. For example, expression in 70N cells, 76N cells or another normal mammary or prostate cell line and no or very low expression in a mammary tumor cell line (e.g., MDA157 cells or 21PT cells). Those skilled in the art will realize that a variety of specific assays can be readily created by choosing appropriate cells.

The invention features purified DNA (for example, cDNA) which includes a maspin transcriptional regulatory sequence, vectors which include a maspin transcriptional regulatory sequence, and cells which include such vectors.

Purified or isolated DNA is DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

A transformed cell is a cell into which (or into an ancestor of which) has been introduced, by means of recombinant DNA techniques, a DNA molecule, e.g., a DNA molecule which includes a maspin transcriptional regulatory sequence.

In one aspect, the invention features an isolated nucleic acid molecule which includes the nucleotide sequence set forth in FIG. 3 from nucleotide −506 to nucleotide −44

(nucleotides 451–914 of SEQ ID NO:1), inclusive (e.g, the nucleotide sequence set forth in FIG. 3 from nucleotide −506 to nucleotide −1 (nucleotides 450–957 of SEQ ID NO: 1), inclusive; the nucleotide sequence set forth in FIG. 3 from nucleotide −956 to nucleotide −1 (nucleotides 1–957 of SEQ ID NO:1), inclusive; or the nucleotide sequence set forth in FIG. 3 from nucleotide −956 to nucleotide +184, inclusive; nucleotides 1–1141 of SEQ ID NO:1).

In another aspect, the invention features a nucleic acid vector (e.g., a plasmid, a virus, or a retrovirus) which includes the above-described isolated nucleic acid molecule.

In another aspect, the vector includes a reporter gene operably linked to the above-described isolated nucleic acid molecule.

In various embodiments the reporter gene is selected from the group consisting of β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacz (encoding β-galactosidase), and xanthine guanine phosphoribosyltransferase (XGPRT).

The invention also features host cells (e.g., a breast cancer cell or a prostate cancer cell) which harbors an above-described vector.

The invention features a method for screening compounds to identify candidate compounds for treatment of prostate cancer, comprising:

(a) providing a host cell comprising an isolated nucleic acid molecule comprising a portion of the maspin promoter region in operative association with a reporter gene;

(b) measuring the expression of the reporter gene in the presence and the absence of a selected compound;

wherein an increase in expression of the reporter gene in the presence of the selected compound compared to expression of the reporter gene in the absence of the selected compound indicates that the selected compound is a candidate compound for treatment of prostate cancer.

The invention also features a method for screening compounds to identify candidate compounds for treatment of breast cancer, comprising:

(a) providing a host cell comprising a nucleic acid molecule comprising a portion of the maspin promoter region in operative association with a reporter gene;

(b) measuring the expression of the reporter gene in the presence and the absence of a selected compound;

wherein an increase in expression of the reporter gene in the presence of the selected compound compared to expression of the reporter gene in the absence of the selected compound indicates that the selected compound is a candidate compound for treatment of breast cancer.

Also within the invention is a method for identifying compounds which increase the expression of maspin, comprising:

(a) providing a host cell comprising an isolated nucleic acid molecule comprising a portion of the maspin promoter region in operative association with a reporter gene;

(b) measuring the expression of the reporter gene in the presence and the absence of a selected compound;

wherein an increase in expression of the reporter gene in the presence of the selected compound compared to expression of the reporter gene in the absence of the selected compound indicates that the selected compound increases expression of maspin.

In various embodiments of these methods, the portion of the maspin promoter comprises the nucleotide −506 to −44, inclusive; and the portion of the maspin promoter region comprises an HRE element having the sequence GTACTCT-GATCTCC (SEQ ID NO:20).

The host cells in screening methods are preferably tumor cells. Thus, candidate compounds for treatment of breast cancer are preferably identified by screening methods employing breast cancer cells as the host cell. Candidate compounds for treatment of prostate cancer are preferably identified by screening methods employing prostate cancer cells.

The invention also features a method for detecting the presence of metastatic prostate epithelial cells in a patient comprising:

(a) obtaining a sample of prostate epithelial cells;

(b) measuring the amount of maspin in the sample of prostate cells;

wherein the presence of a higher than normal amount of maspin indicates the presence of metastatic prostate epithelial cells.

Ausubel et al. (Current Protocols in Molecular Biology, John Wiley & Sons, New York, 1994) describes a number of suitable reporter genes and assays which can be used to measure their expression.

BRIEF DESCRIPTION OF THE DRAWINGS

FIG. 1 is a photograph of the results of Northern analysis of maspin expression in mammary epithelial cells. Cell lines 70N and 76N are normal, human mammary epithelial cell lines are. Cell lines 56NF1 (mammary fibroblast cell line), FS2 (foreskin fibroblast cells), and U937 (human monocytic cells) are of non-epithelial origin. Hela is a cervical carcinoma. All others cell lines noted in this figure are human breast tumor cell lines. Each lane contains 20 μg of total RNAs. The blots were hybridized with 2.5 kb maspin cDNA probe. 36B4 was used as loading and transfer control.

FIG. 2 is a photograph of the results of Northern analysis of maspin expression in human tissue blots. The blots were from Clontech™, Inc. (Palo Alto, Calif.; Human MTN blot 1 #7760 and Human MTN blot 2 #7759). Each lane contains 2 μg poly A+ RNA from human tissues. 36B4 and actin were used as loading controls.

FIG. 3 depicts the sequence of the promoter region and partial cDNA of maspin (SEQ ID NO:1). The major transcription start is numbered +1. The putative regulatory elements (AP1, AP2, Ets, and HRE) are boxed.

FIG. 9A is a schematic depiction of various deletion constructs used to analyze regulation of the maspin gene. The top line indicates the position of a number of putative recognition elements for transcription factors. The other lines represent deletion constructs.

FIG. 12A is a schematic representation of a number of CAT constructs.

FIG. 12B is a graph depicting the results of CAT assays employing the constructs depicted in FIG. 12A. The constructs were introduced into LNCAP cells or CF3 cells. Extracts were assayed for CAT activity, and relative activity was determined by normalizing to pKTCAT.

DESCRIPTION OF THE PREFERRED EMBODIMENTS

Figure 4:
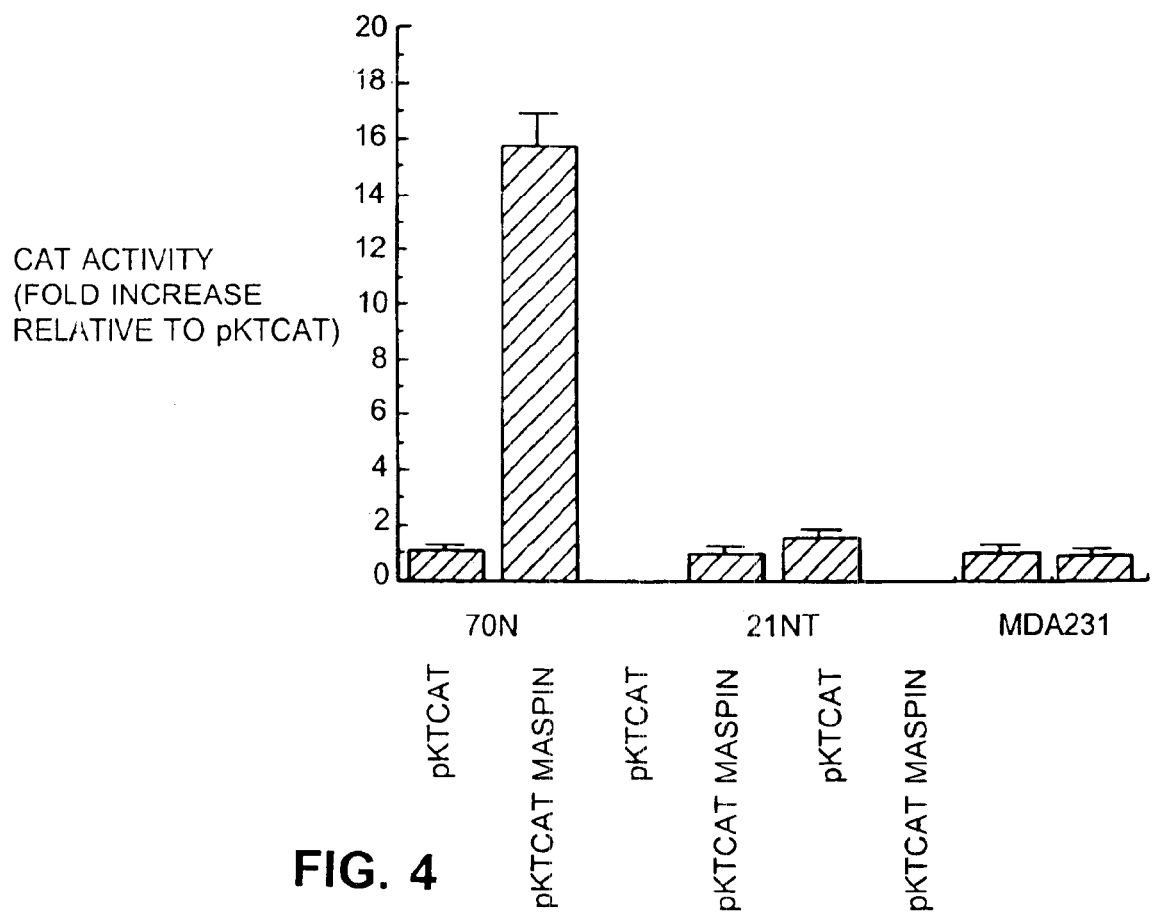
FIG. 4 is a graph depicting the results of CAT assays of pKT(956) in 70N, 21NT, and MDA231 cells. Plasmid pKT(956) was transfected into three cell lines along with a negative control pKTCAT and a positive control PCMV-CAT. Extracts of 20 units were assayed for CAT activity. The activity was normalized to pKTCAT control. Values are obtained from 5 repeated experiments. Error bars are standard errors.

The studies described below characterize the transcriptional control elements associated with the maspin gene. Among other things, these studies demonstrate that expression of maspin is regulated at the transcriptional level. These studies suggest that a factor binding to a Ets regulatory element activates transcription of maspin in normal mammary epithelial cells. Among other things, these studies demonstrate that the enhancing function of the Ets element is not observed in breast carcinoma cells; that deletion of the Ets element abolishes promoter activity in normal cells; that the Ets element cooperates with a downstream element, possibly an AP1 site, to activate maspin transcription; and that a protein factor(s) binds to the Ets element. In addition, these studies indicate that expression of maspin is both tissue and cell specific. The maspin gene is not expressed in heart, brain, placenta, lung, liver, skeletal muscle, kidney, and pancreas.

The following procedures and materials were employed in experiments described below.

Cell lines and media

Normal human epithelial cells 70N, 76N, and 81N were from reduction mammoplasties as described by Band et al. (Proc. Natl. Acad. Sci. U.S.A., 86:1249, 1989). Tumor cell lines were obtained from the American Type Culture Collection®(Bethesda, Md.). Cell lines in the 21T series were derived from a single patient's tumor cells and are representative of tumor progression. Both normal and tumor cells were cultured in DFCI-1 medium as described by Band et al. (Proc. Natl. Acad. Sci. U.S.A., 86:1249, 1989).

Northern blot analysis

Total cellular RNA was prepared as previously described (Swisshelm et al., Cell Growth & Differ., 5:133, 1994). Briefly, 20 μg of total RNA was fractionated on 1% agarose-1.7 M formaldehyde gels, transferred to Zetaprobe membrane (BioRad™) in 20x SSC, and baked for 1 hr at 800 C. Blots were probed with a 2.5 kb EcoR1/Xhol fragment from the maspin cDNA plasmid. 36B4 was used as an internal loading and transfer control.

Promoter cloning and sequencing

A YAC genomic DNA clone library was screened according to standard techniques with 32P end labeled antisense OL1 as a probe. A positive clone was identified and subcloned into pBluecriptSK™ vector to generate pSKmas1 plasmid. The pSKmas1 was partially sequenced to confirm the presence of promoter, exon 1, and the intron 1 boundary. DNA sequencing was performed using ABI™ 373A Automated DNA sequencer at the core facility of Dana-Farber Cancer Institute.

Oligonucleotides

Oligonucleotides were synthesized by Amitof, Inc (Boston, Mass.). OL1: TCACCAGTTATCCTGGAAAAT-GCGTGGAAAAGGAACAGGCAAGCGAGGAGC (SEQ ID NO: 2)was used for cloning and primer extension.

For electrophoretic mobility shift assay experiments, pairs of sense and antisense oligonucleotides were mixed in equimolar amounts and annealed in 10 mM Tris (pH 8.0), 200 mM $NaCl_2$, 1 mM EDTA by heating to 95° C. for 5 min and cooling to room temperature over an period of 3 hours. The following oligonucleotides were used: Ets wild-type (WT) sense oligonucleotide CAGCCCCTTCCTGC-CCGAAC (SEQ ID NO: 3); Ets wild-type (WT) antisense oligonucleotide GTCGGGGAAGGACGGGGCTTG (SEQ ID NO: 4) Ets mutant (MT) sense oligonucleotide for competition CAGCCCCTTTTTGCCCGAAC (SEQ ID NO: 5); Ets mutant (MT) antisense oligonucleotide for competition GTCGGGGAAAAACGGGCTTG (SEQ ID NO: 6); non-specific (NS) sense olgonucleotide for competition CCTTGTCAGACAGGCAAGTGCC (SEQ ID NO: 7); non-specific (NS) antisense olgonucleotide for competition GGAACAGTCTGTCCGTTCACGG (SEQ ID NO: 8)

Primer extension analysis

A OL1 primer corresponding to sequence from nucleotide +140 to nucleotide +89 was 5' end-labeled with $^{32}P$ and used in primer extension experiments. Total RNA from 70N cells was isolated as described by Swisshelm et al. (Cell Growth & Differ. 5:133, 1994). OL1 was $^{32}$P-labeled, and hybridized with 20 μg of total RNA, and then extended using reverse transcriptase. The products were separated on a 6% PAGE gel. An M13 single stranded DNA sequencing product was run in parallel as a reference to determine the size of primer extended products.

Constructs

The pSKmasl was digested with TthIII (at nucleotide +87), blunt ended with T4 DNA polymerase, and ligated to HindIII linkers. Subsequent digestion with HindIII (at nucleotide +87) and XbaI (at nucleotide −956) generated a XbaI-HindIII fragment containing the promoter, which was directionally subcloned into pKTCAT promoterless vector to generate pKT(956). Progressive deletion of pKT 956) were made either by restriction enzyme digestion or by exoIII treatment. Plasmids pKT(956), pKT(297), pKT(136), pKT(90) were generated by enzyme digestion of pKT(956) and removing the fragments of Pst-Pst, Xba-Pst, Xba-Snab, Xba-Stu respectively. The linearized DNAs were blunt ended with T4 DNA polymerase and ligated. Plasmid pKT (265), pKT(172), and pKT(17) were generated by digestion of pKT(956) with SmaI and XbaI, followed by exoIII treatment. The linearized DNAs were filled by Klenow and then ligated. The exoIII deletion constructs were sequenced to confirm the site of deletion.

For the construction of Ets3CAT and Ets3/APlCAT, a fragment corresponding to nucleotide −120 to nucleotide +140 bp was prepared by PCR using OL1 antisense oligonucleotide and Ets WT sense oligonucleotide. To create Ets3CAT, the PCR fragment was cloned into PCRII vector with SacI flanking the Ets site. The resulting plasmid was digested with SacI and StuI to generate a Sac-Stu fragment containing the Ets element (nucleotide −120 to nucleotide −90). This fragment was subcloned into pBLCAT2 at the SacI and SmaI sites to generate Ets3CAT.

To generated Ets/APICAT the PCR product was digested with BglI (at +10 bp), filled by T4 DNA polymerase, and then digested with SacI. The Sac-Bg1 fragment (nucleotide −120 to nucleotide +10 (including the AP1 site at nucleotide −53) was subcloned into pBLCAT2 at SacI and SmaI to generate Ets/AP1CAT.

Plasmid 2xEtsCAT was generated by digestion of pKT (956) with StuI, and subcloning of StuI-StuI fragment (nucleotide −511 to nucleotide −90) into the pBLCAT2 SmaI site.

All constructs were sequenced to confirm the presence of fragments in single copy.

Transfection and CAT assay

For CAT assays cells were plated at 1.0x106/p100 and grown to about 75% confluence. DNA was transfected by the method of modified DEAE-Dextran (Promega, Madison, Wis.). The cells were transfected with 10 μg reporter plasmid (except for pCMVCAT where only 2 μg of DNA was used) and 1 μg of pCMVβgal (internal control for transfection efficiency). Forty-eight after transfection cells were harvested in 0.25 M Tris(pH 8.5)−15% glycerol and extracts were prepared by three cycles of freeze-thawing. The β-galactosidase activity in the extracts was measured using standard techniques and 20 units of extract were used for each CAT assay (except for the pCMVCAT positive control where only 10 units of extracts were used because of high activity). CAT assay was performed as described by Gorman et al. (Mol. Cel. Biol.,2:1044, 1982). Acetylated chloamphenicol and nonacetylated chloramphenicol was quantitated by cutting out the appropriate regions of the silica gel TLC plate and counting in BioFlour™(DuPont; Wilmington, Del.)

Electrophoretic mobility shift assay experiments

Whole cell extracts were made by a modification of that described by Dignam et al. (Nucleic Acid Res. 11:1475). Binding reactions were carried out at room temperature for 15 min in 4% glycerol, 1 mM MgCl$_2$, 0.2 mM EDTA, 0.5 mM DTT, 50 mM NaCl$_2$, 10 mM Tris-Cl, 2 μg poly dI-dC, 10 μg to 30 μg cellular extract, and end-labeled oligonucleotide probe. The complexes were subjected to electrophoresis at 5% acrylamide gel in 0.5x Tris-borate-EDTA buffer.

Tissue and cell specific expression of maspin

The maspin gene was originally isolated from normal mammary epithelial cells. To understand the tissue expression pattern and the cell specificity of maspin, we performed northern blot analysis with RNAs from several human cell lines as well as a tissue blot (Clontech) containing RNAs from human tissues. The results of these experiments reveal that maspin is highly expressed in 70N and 76N normal mammary epithelial cells, downregulated in 21NT and 21PT primary tumors, and silent in a series of invasive tumor cells (FIG. 1). The gene is not expressed in cells of non-epithelial origin, such as 56NF1 (mammary fibroblast cells), FS2 (foreskin fibroblast cells), and U937 (human monocytic cells). Interestingly, it is expressed at low level in Hela cells, which are cervical carcinoma derived cells of epithelial origin.

Maspin RNA was not expressed in heart, brain, placenta, lung, liver, skeletal muscle, kidney, pancreas, spleen, ovary, colon, and leukocyte, but was expressed in prostate, thymus, testis, and small intestine. Some of these results are shown in FIG. 2. These results identify maspin as a tissue-and cell type specific gene, well expressed in normal mammary epithelial cells.

Cloning and sequencing of the upstream promoter

In an attempt to identify the maspin promoter, a genomic DNA library was screened with $^{32}$p labeled maspin cDNA probe. This approach failed to identify the first exon of maspin.

Subsequently we screened genomic DNA using a YAC clone containing a cluster of serpins including maspin. This screening was performed using a 50 mer oligonucleotide, OL1, (TCACCAGTTATCCTGGAAAATGCGTGGAAA-AGGAACAGGCAAGCGAGGAGC; SEQ ID NO. 2) from the 5' untranslated region of maspin. A positive clone was identified containing a 1.2 kb 5' -flanking region, a 9 kb intron (intron 1), and partial exon 2 sequence. A substance was isolated partial sequencing of a selected subclone revealed that it included exon 1, nucleotides +1 to +184, and an upstream region of maspin (FIG. 3; SEQ. ID NO: 1). The genomic DNA sequence from +115 to +184 nucleotides is identical to the CDNA sequence in that region. Exon 2 starts at nucleotide +185, 23 bp 5' upstream of an ATG site. Analysis of the upstream region of maspin gene revealed the presence of a number of potential transcription regulatory sites, discussed below.

Primer extension analysis using OL1 the oligonucleotide which is complementary to the first exon, was performed to localize the transcription initiation site. This analysis identified multiple start sites. The major primer-extended product (which extends 127 nt) was designated as nucleotide +1 site. We also identified two minor products extending to −10 bp and +14 bp respectively. No TATA box was found in the vicinity, indicating that maspin has a TATA-less promoter.

A 1 kb upstream region is sufficient for activating transcription of maspin in normal breast cells We identified potential recognition sites for several transcription factors in the maspin promoter region:Ets regulatory element sites, AP1 recognition sites, an AP2 recognition site, and a HRE recognition site are all located within 1 kb of the putative transcription start site (FIG. 3). To determine whether this 1 kb upstream region of the maspin gene is sufficient for activating transcription, a 1043 bp fragment (−956 to +87) of the maspin gene was fused to the CAT gene to generate pCAT(956).

The PCAT(956) construct was transfected into normal mammary epithelial cells (70N), primary tumor cells (21NT), and metastatic tumor cells (MDA231). CAT activity was assayed and normalized to pKTCAT, an essentially promoterless negative control. The results of this analysis are present in FIG. 4.

Activity of the pCAT(956) construct was 15.6 fold high than PKTCAT activity in 70N cells, 2-fold lower than pKTCAT activity in 21NT cells, and undetectable in MDA-MB231 cells. When a CMV-CAT positive control vector was transfected into 70N cells, the activity was about 50-fold higher than that observed with pCAT(956). The same maspin promoter is about 8-fold stronger in 70N than in the 21NT cells.

These results are consistent with mRNA levels measured by Northern blotting. For example, the level of maspin mRNA in the primary breast tumor cell line 2.1NT was approximately 10% of the level in 70N normal cells. As can be seen in FIG. 1, maspin mRNA was undetectable in metastatic tumor cell lines MDA157, MDA435, MDA436, MCF7, T47D, ZR75, BT549. These data indicate that maspin exogenous promoter strength mimics the endogenous RNA expression level, and that the approximate 1 kb region of the maspin gene inserted into pCAT(956) includes significant features of the maspin promoter.

Functional Analysis of Maspin Promoter

Figure 5:
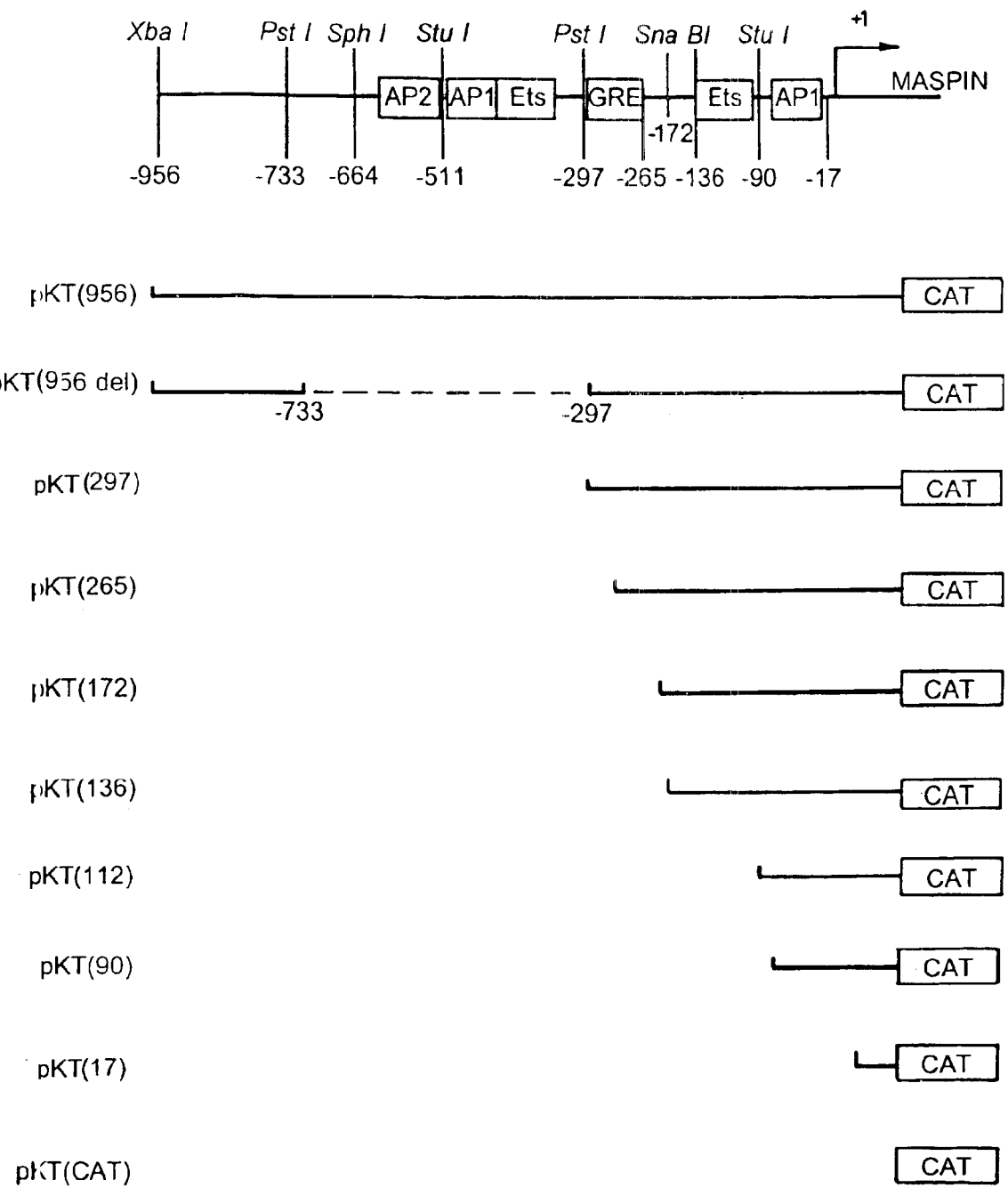
FIG. 5 is a schematic depiction of various deletion constructs used to analyze regulation of the maspin gene. The top line indicates the position of a number of putative recognition elements for transcription factors. The other lines represent deletion constructs.

In order to identify functional maspin promoter elements, progressive deletion mutants were constructed. Deletion constructs were transfected into 70N normal mammary epithelial cells and MDA231 tumor cells, and their relative CAT activities were assayed. The various constructs are depicted schematically in FIG. 5. The CAT activity of these constructs is presented in FIG. 6 in which CAT activity is expressed relative to that of pKTCAT in the same cells.

Deletion of nucleotides −956 to −386, which removes the distal Ets site, did not significantly change the activity. Further deletion up to position −136 bp, or −112 bp also did not alter the activity significantly despite the fact that well-known elements are present in this region, including the distal sites Ets, AP2, and HRE. However, deletion from nucleotide −112 bp to nucleotide −90 bp, which removed the proximal putative Ets recognition element, completely abolished the CAT activity of 70N extracts. The level of pKT(90) was comparable to that of the negative control vector, which does not contain a functional promoter. These results demonstrate that the proximal Ets site is the major positive cis element within the 1 kb proximate region responsible for up-regulation of maspin in normal mammary epithelial cells.

Figure 6:
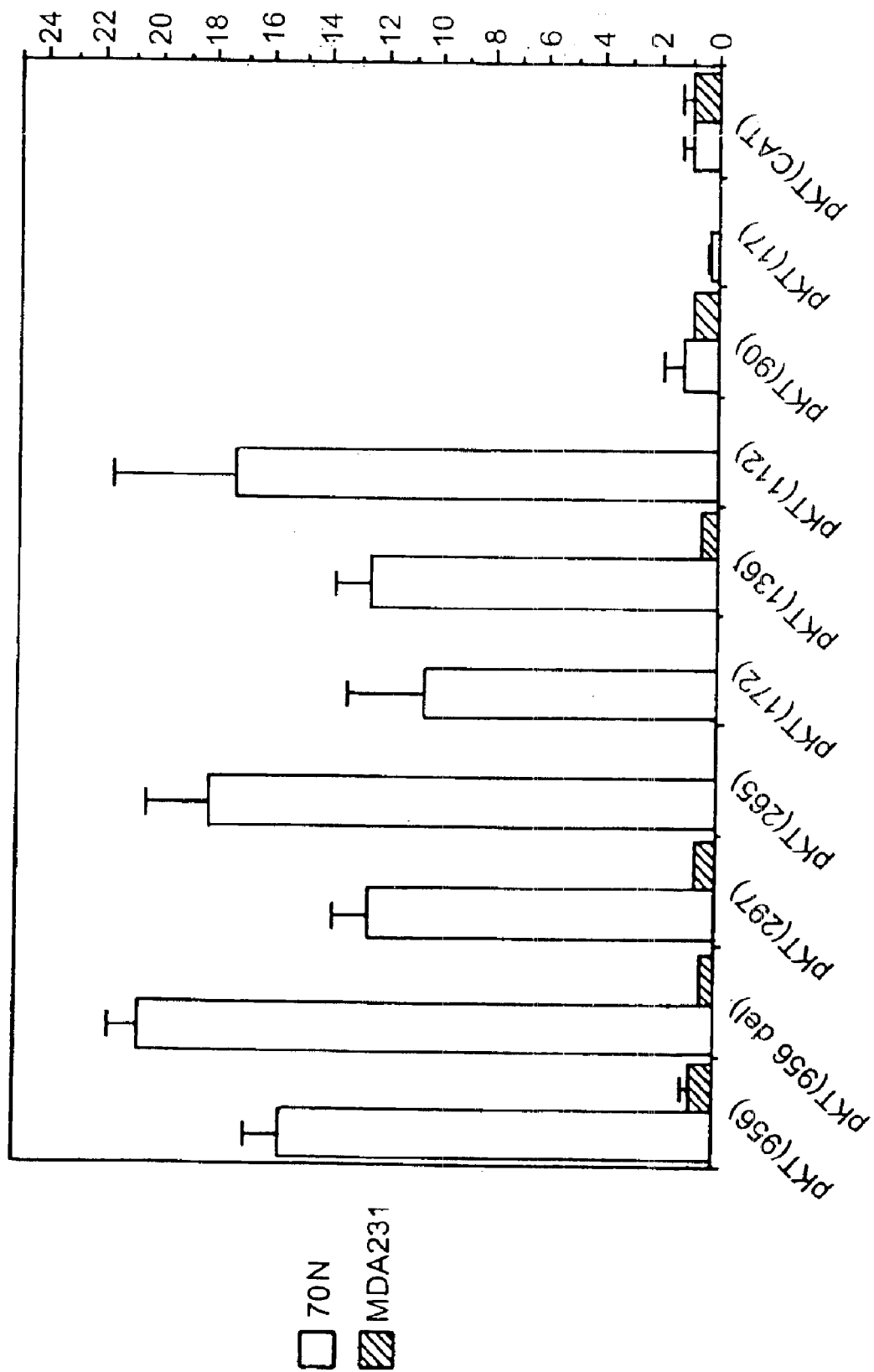
FIG. 6 is a graph depicting the results of CAT assays of various deletion constructs. The CAT constructs were transfected into 70N and MDA231 cells. Extracts of 20 units were assayed for CAT activity. Relative activity is determined by normalizing to pKTCAT. Error bars are obtained from at least four repeated experiments. Values without error bar from some constructs transfected to MDA-MB231 are obtained from repeated experiments.

These constructs were also tested in breast carcinoma MDA 231 cell extracts (FIG. 6). None of the deletion constructs resulted in CAT activity significantly higher than that of negative control vector, demonstrating that tumors were unable to activate transcription. These results suggest that the down-regulation of the maspin gene in MDA231 cells is unlikely to be due to negative cis elements.

Ets Cooperates with Other Promoter Elements

Figure 7:
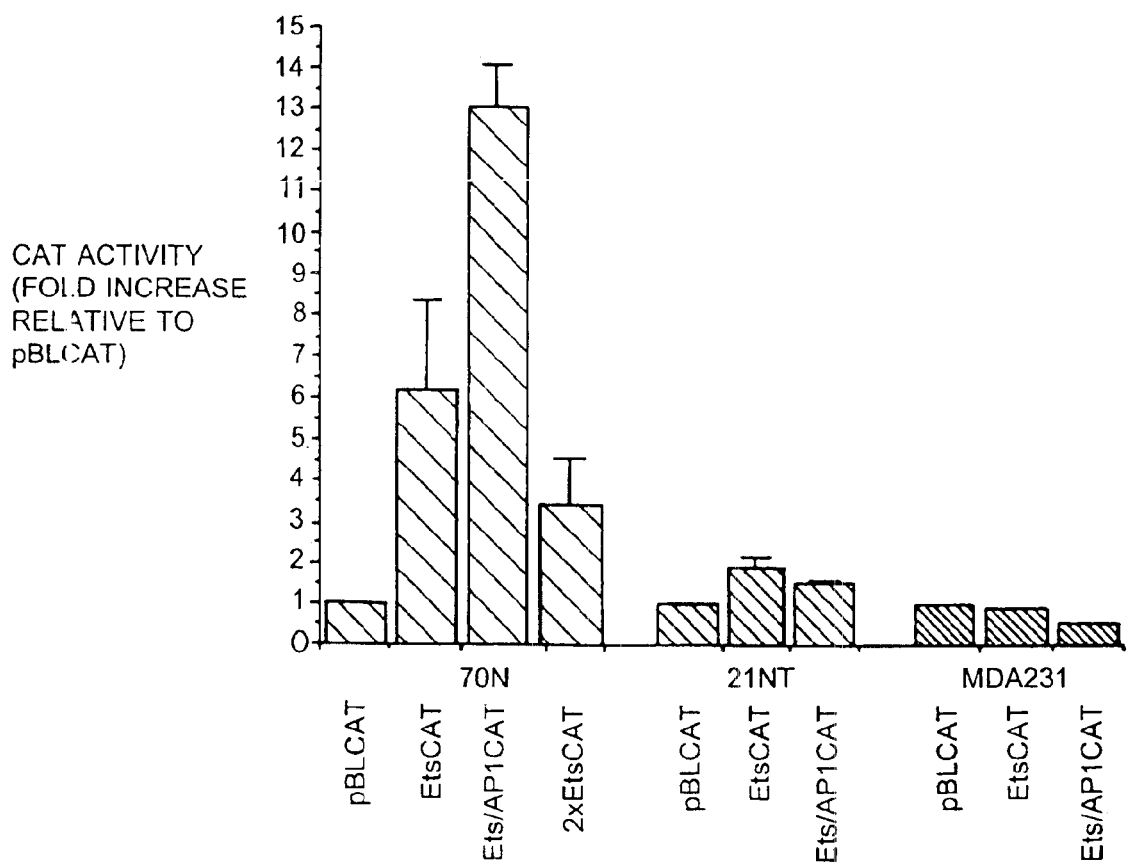
FIG. 7 is a graph depicting the rests of CAT assays of Ets constructs in 70N, 21NT, MDA231 cells. CAT activity was normalized to a PBLCAT control. Values are obtained from at least three repeated experiments. Error bars are standard errors. Data from MDA231 are average of two repeated experiments.

To further confirm that the Ets element is involved in transcriptional activation of maspin, we investigated the ability of Ets to enhance transcription by cloning the Ets site (nucleotide −112 to nucleotide −90 ) into the pBLCAT2 vector, which includes the minimal thymidine kinase promoter, but no enhancer. To test the possibility of cooperative interaction between Ets and other cis elements in the promoter, we separately subcloned a first fragment (nucleotide −120 to nucleotide +10) containing the proximal Ets and AP1 sites and a second fragment (nucleotide −526 to nucleotide −90) containing both Ets sites into pBLCAT2 to generate Ets/AP1CAT and 2xEtsCAT. These constructs were transfected into 70N cells, 21NT cells, and MDA231 cells. As shown in FIG. 7, the presence of the proximal Ets site greatly increased the CAT activity of pBLCAT2 in 70N. The 2XEtsCAT construct did not give higher activation than the EtsCAT construct. However, the Ets/AP1CAT construct had a several fold higher activation than EtsCAT, indicating cooperative interaction between PEA3 and other elements, probably AP1. The enhancer effect of the putative Ets element was decreased for both EtsCAT and Ets/AP1CAT in 21NT cells. No enhancing function was observed in MDA231 cells.

To test the role of the Ap1 site in the maspin promoter, we subcloned the fragment containing the proximal Ets and AP1 sites (−112 to −48 bp) and the one containing the Ets site and mutated Ap1 site into pBLCAT2 to generate pEts/Ap1CAT and pEts/mAp1CAT. To test the effect of Ets mutation on transcriptional activation, we mutated the Ets site in the pEts/Ap1CAT construct to generate pmEts/Ap1CAT. These constructs were transferred into 70N, 21NT, and MDA231 cells. These studies revealed that the presence of the proximal Ets site greatly increased the CAT activity of pBLCAT2 in 70N. The mutation at the Ets site abolished the activity. The pEts/Ap1CAT construct had a dramatic increase in transcription activation over pEtsCAT alone, whereas pEts/mAP1CAT has the same range of activity as pEtsCAT. These data demonstrate that Ets alone is sufficient to activate transcription, Ap1 is involved in transcriptional activation of maspin in 70N cells, and that Ap1 cooperates with Ets in this process.

The enhancing ability of Ets was decreased for pEtsCAT in 21NT cells, indicating the impaired transcriptional activation through the Ets site in the primary mammary tumor cells. Moreover, the cooperative transactivation between Ets and Ap1 was lost in 21NT cells. Both transactivation through Ets and cooperation between Ets and Ap1 were lost in metastatic MDA-MB231 cells.

Proteins binding to the Ets Element are Different in Normal and Tumor Cells

The electrophoresis mobility shift assay provides a simple, sensitive method for the detection of sequence-specific DNA binding proteins in crude extracts. Proteins that bind specifically to an end-labeled DNA fragment retard the mobility of the fragment during electrophoresis, resulting in discrete bands corresponding to the individual protein-DNA complexes. To confirm the presence of Ets recognition element binding activity, oligonucleotides corresponding to the Ets element region were end-labeled and used in electrophoresis mobility shift assay experiments (EMSA) with whole cell extracts from 70N normal epithelial cells, primary tumor 21NT cells, and MDA231 cells.

Figure 8:
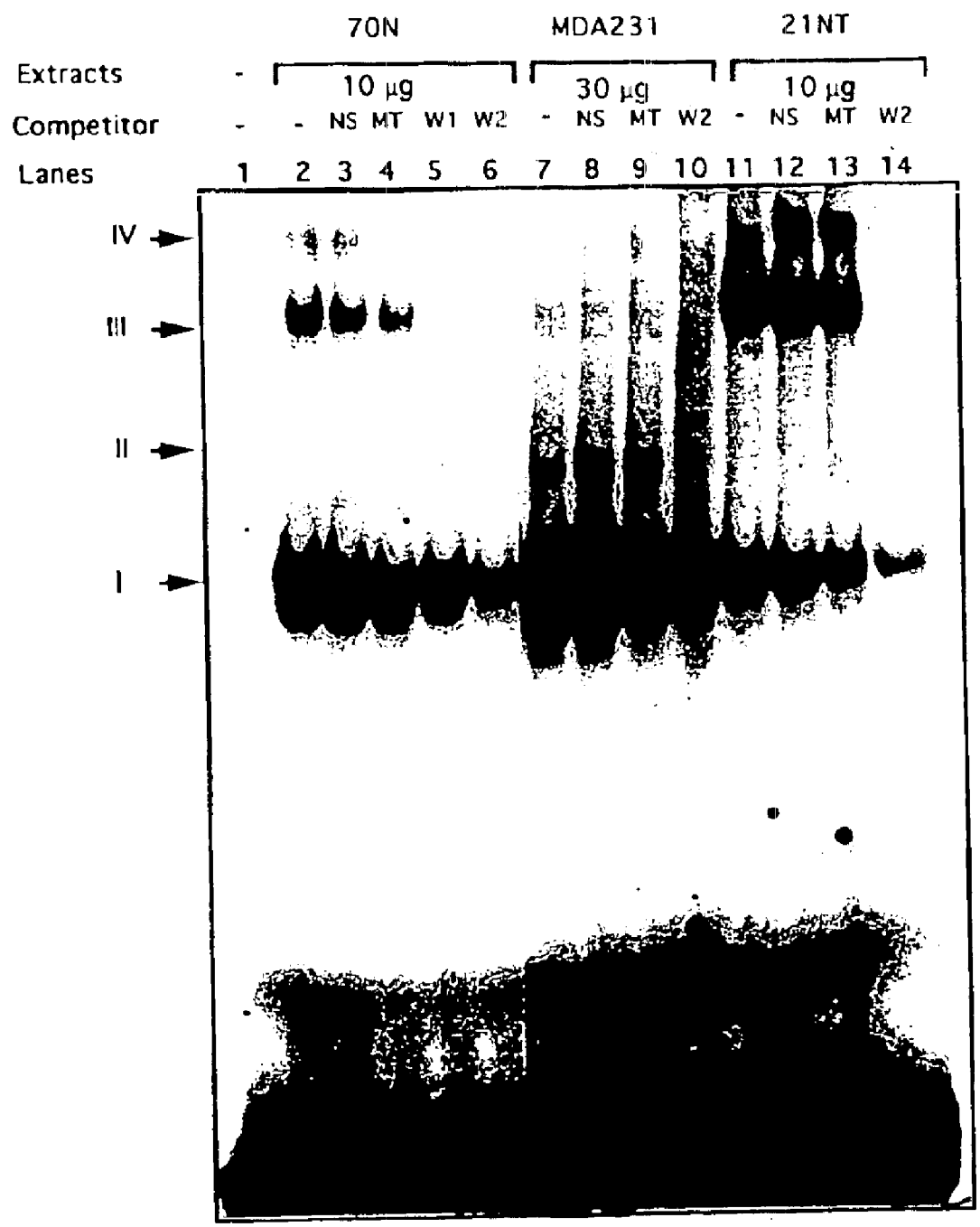
FIG. 8 is a photograph of the results of electromobility shift assays. The end labeled oligonucleotides were incubated without extract (lane 1) or with extracts from 70N cells (lane 2–6), MDA231 (lane 7–10), or 21NT cells (lane 11–14). Arrowheads point to the different DNA-protein complex, I, II, III, IV. Competition was carried out with 300X non-specific oligonucleotides (lane 3, 8, 12), 300X mutant Ets oligonucleotides (lane 4, 9, 13), 60X (lane 5) unlabeled wild-type Ets oligonucleotides, or 300X (lane 6, 10, 14) unlabeled wild type Ets oligonucleotides.

As shown in FIG. 8, four different DNA-protein complexes (I–IV) were identified. A common complex I was formed in extracts from all cell lines. Complexes III and IV were similar using extracts from 70N and 21NT cells, whereas little or no such complexes were observed with an excess amount of extract from MDA231. An additional complex II was observed only with extracts from MDA231 cells.

All of the bands were specific, since both non-specific oligonucleotides (NS) and specific oligonucleotides with mutations in the Ets site (MT) could not compete for the binding (lanes 3, 4, 8, 9, 12, 13), while an excess amount of unlabeled Ets wildtype oligonucleotide (W1, W2) competed well for the binding (lanes 5, 6, 10, 14).

These results demonstrate the presence of Ets recognition element binding complexes in all 3 cell types. However, complexes III and IV are observed in 70N and 21NT cell extracts, which are transcriptionally active; while complex II is only present in extracts from inactive MDA231 cells.

Regulation of the Maspin Gene

The mammary gland undergoes structure and biochemical changes continuously from embryo to aging females. Several well-known milk proteins, such as whey acidic protein, lactoalbumin, lactoglobulin, are considered as markers for the differentiated function of the mammary epithelium (Mink et al., Mol. and Cell. Biol. 12:4906, 1991). A mammary cell specific enhancer (the binding site for Mammary cell Activating Factor or MAF) has been identified in the promoter of several milk genes (Mink et al., Mol. and Cell. Biol. 12:4906, 1991).

We have compared the consensus binding sequence of MAF with that of Ets and found that they share a core binding sequence AGGAAT, which is considered to be the binding site for Ets family transcriptional binding proteins (Werner et al. Cell 83:761, 1995; Wasylyk et al., Nature 346:191, 1990). Therefore, MAF may belong to the Ets family. This possibility is supported by the EMSA experiment in which MAF binding complexes were competed by several high affinity Ets-binding sites recognized by the majority of the known members of Ets family (Welte et al., Eur. J. Biochem. 223:997, 1994).

The maspin promoter contains two Ets elements. CAT assays indicated that the proximal Ets element mediates the cell type specific expression in human mammary epithelial cells. These results suggest that maspin, which is well expressed in mammary gland, may be regulated by an upstream element important for regulation of milk genes. This would suggest that maspin can serve as a marker for mammary gland and mammary cell differentiation. Moreover, the tissue and cell type specific expression pattern of maspin suggest a specific role for maspin in mammary gland development, in addition its role in tumor invasion and metastasis.

The members of the Ets family of transcription factors of this gene family have a conserved DNA binding domain that binds the consensus sequence (GGA(A/T)(Current et al., Cell 55:395, 1988; Macleod et al., Trends Biochem. Sci. 17:252, 1992). Binding of ETS protein is often associated with the binding of other proteins, and it is thought that binding of other proteins to the ETS protein may stabilize the interaction between ETS DNA binding domain and DNA (Petersen et al., Science 269:1866, 1995). On the other hand, the binding protein may serve as coactivator. For example, JUN and PNT, a Drosophila ETS protein, act synergistically to activate the promoter containing Ap1/Ets elements in the R7 photoreceptor induction (Treier et al., Cell 83:753, 1995). In addition, SAP1, a ETS protein, interacts with SRF in the c-fos promoter (Dalton et al., Cell 68:597, 1992). Recently, the three dimensional structure of ETS1, a founding member of the ETS family has been resolved (Dalton et al., Cell 68:597, 1992). Binding of ETS1 to DNA results in a sharp kink of 60° and local widening of the minor groove in the DNA. This structure change leads to the hypothesis that ETS1, like many DNA bending proteins such as SRY, LEF1, are involved in the architecture of protein-protein interaction (Dalton et al., Cell 68:597, 1992; Love et al., Nature 376:791, 1995). These so-called "architectural proteins" can sculpt many protein clusters into precise three dimensional shapes to activate transcription (Wickelgren, Science 270:1587, 1995).

Certain other features of the maspin gene are noteworthy. First, cloning and sequencing of maspin promoter reveal the presence of multiple regulatory cis elements: Ets, Ap1, Ap2 and HRE. Apparently, not all of them mediate transcription activation in normal mammary epithelial cells; however, they may be involved in other types of regulation during mammary gland development. Second, there is no apparent TATA box in the maspin promoter. Primer extension analysis identified multiple start sites which are characteristic of TATA-less promoters. Third, maspin belongs to the serine proteinase inhibitor superfamily located at chromosome 18q3.5. Others have shown that a cluster of serpins, including maspin, scca1 and scca2, and pai2 are located in the same chromosomal region (Schneider et al., Pro. Natl. Acad. Sci. USA 92:3147, 1995). Because the genes are closely linked, they may have evolved by gene duplication. Thus, the regulation of other genes in this cluster (e.g., the scca1 and scca2 genes) may be similar to that of maspin.

It should also be noted that immunostaining of normal and tumor specimens from surgery is consistent with these results at the protein level. Moreover, maspin expression decreased with increasing malignancy of primary tumors, and was absent from lymph node and distant metastases.

Regulation of Maspin Expression in Prostate Cells

Maspin is expressed in normal prostate epithelium. The experiments described below demonstrate that maspin expression is down-regulated in metastatic prostate cells and that prostate expression of maspin is regulated by both positive and negative elements at the transcriptional level.

Materials and Methods

The following materials and methods were used to investigate maspin expression in normal prostate cell lines and tumor cell lines.

Cell Lines

Normal human prostate epithelial cells (HPECs) (CF3, CF91, MLC) were obtained from Dr. John Rhim (NIH). Tumor cell lines LNCaP, PC3, and DU145 were obtained from the American Type Culture Collection (Bethesda, Md.). Normal cells were cultured in keratinocyte medium supplemented with 5 ng/ml EGF. Tumor cells were cultured in RPMI-1640 media supplemented with 10% FBS.

Northern Blot Analysis

Total cellular RNA was prepared using standard techniques. 20 µg of total RNA was fractionated on 1% agarose- 1.7M formaldehyde gels, transferred to Zetaprobe® (Bio-Rad™) membranes in 20xSSC, and baked for 1 hr at 80 EC. Blots were probed with a 2.5 kb EcoR1/XhoI fragment from the maspin cDNA plasmid. 364B4 was used as an internal loading and transfer control (Laborda et al., Nucl. Acids. Res. 19:3998, 1991).

Oligonucleotides

Oligonucleotides were synthesized by Amitof, Inc. (Boston, Mass.). For annealing, pairs of sense and antisense oligonucleotides were mixed in equimolar amounts and annealed in 10 mM Tris (pH 8.0)–200 mM NaCl–1 mM EDTA by heating to 95° C. for 5 min and cooling to room temperature over a period of 3 hours.

For EMSA Experiments:

Maspin HRE:

sense (OL1') AGTACTCTGATCTCCATTC (SEQ ID NO: 9) antisense (OL2') GAATGGAGATCAGAGTACT (SEQ ID NO: 10)

Consensus HRE for Competition sense (OL3') CTAGGCTGTACAGGATGTTCTGC-CTAG (SEQ ID NO: 11)

antisense (OL4') GATCCGACATGTCCTACAAGACG-GATC (SEQ ID NO: 12)

Non-specific Oligonucleotide (NS) for Competition sense (OL5') CCTTGTCAGACAGGCAAGTCC (SEQ ID NO: 13)

antisense (OL6') GGAACAGTCTGRCCGTTCACGG (SEQ ID NO: 14)

For PKT(297 mHRE) Construction sense (mHRE) AACTGCAGTTTACACAAAAAGAAT-GATATCCGGAGTAC (SEQ ID NO: 15)

antisense (OL7') GGTGGTATATCCAGT-GATTTTTTTCTCC (SEQ ID NO: 16)

For PBLAp1/HRE Construction sense (OL8') GATCCAGTACTCTGATCTCCATTCG (SEQ ID NO: 17)

antisense .(OL9') GATCCGAATGGAGATCAGAG-TACTG (SEQ ID NO: 18)

Constructs

The pKT series vectors and pEtsCAT were constructed as described above. For the pKT297 mHRE construct, a PCR fragment (using OL7'/mHRE oligos and pKT(297) as the DNA template) was digested with HindIII and Xba1 and subcloned into the Xba1 and HindIII of pKTCAT promoterless vector.

For construction of pBLAp1/HRE, pairs of OL8 and OL9 oligos were annealed as described above. The annealed product was phosphorylated by T4 polynucleotide kinase, and ligated to the BamHI site of pBLAp1 (pBLCAT2 containing three copies of Ap1) to generate pBLAp1/HRE (FIG. 12).

Transfection and CAT assay

Cells were plated at 1 ×106/p100 and grown to about 75% confluence. SNA was transfected by the method of modified DEAE-Dextran (Promega, Inc., Madison, Wis.). The amounts of DNAs used were: 10 μg reporter plasmid, except for PCMVCAT in which only 2 μg of DNA was used. 1 μg of pCMVβgal was used as an internal control for transfection efficiency. For the androgen treatment, 50 nM methyltrienolone.(R1881, from Du Pont-New England Nuclear, Inc., Boston, Mass.) or vehicle was added to the cultures after transfection. Forty eight hrs after transfection, cells were harvested in 0.25 M Tris(pH 8.5)–15% glycerol. The extracts were made by three cycles of freeze-thaw. The β-galactosidase activity in the extracts was calculated as described by Swisshelm et al. (Cell Growth Differ. 5:133, 1994). Twenty units of extracts (calculated by β-galactosidase activity) were used for each CAT assay except for transfection with pCMVCAT positive control in which only 10 units of extracts were used because of high activity. CAT assay was performed as described by Gorman-et al. (Mol. Cell. Biol. 2:1044, 1982). Quantitation of acetylated CoA and nonacetylated chloramphenicol was performed by cutting out the appropriate regions of the silica gel TLC plate and counting in BioFluor (DuPont, Wilmington, Del.).

Electromobility Shift Assay Experiments

Nuclear extracts were made as described by Dignam et al. Nucl. Acids Res. 11:1475, 1983. Binding reactions were carried out at room temperature for 30 minutes in a mixture containing 4% glycerol, 1 mM MgCl2, 0.2 mM EDTA, 0.5 mM DTT, 50 mM NaCl, 10 mM Tris-Cl, 2 μg poly (dI-dC), 50 nM R1881, 10 μg nuclear extracts, and end-labeled oligonucleotide probe. Monoclonal (rat) anti-androgen receptor antibody (MAI-150) was purchased from Affinity Bioreagents, Inc. Antibody against glucocorticoid receptor was purchased from Santa Cruz Biotechnology, Inc. Rat IgG negative control was purchased from Sigma. The complexes were subjected to electrophoresis at 5% acrylamide gel in 0.5 x Tris-Borate-EDTA buffer.

Maspin is Down-Regulated in Prostate Tumor Cells

To understand whether the expression pattern of maspin is altered during prostate tumorigenesis, we performed Northern blot analysis with RNAs from several human normal prostate and tumor cell lines. These experiments revealed that maspin is highly expressed in CF3, CF91, and MLC normal prostate epithelial cells, and down-regulated in LNCaP, PC3, and DU145 prostate tumors. This expression pattern is similar to the findings in the normal mammary epithelial cells and carcinomas, indicating that the down-regulation of maspin expression is a common phenotype of both breast and prostate tumors.

Functional Analysis of the Maspin Promoter in Prostate Cells

Figure 9B:
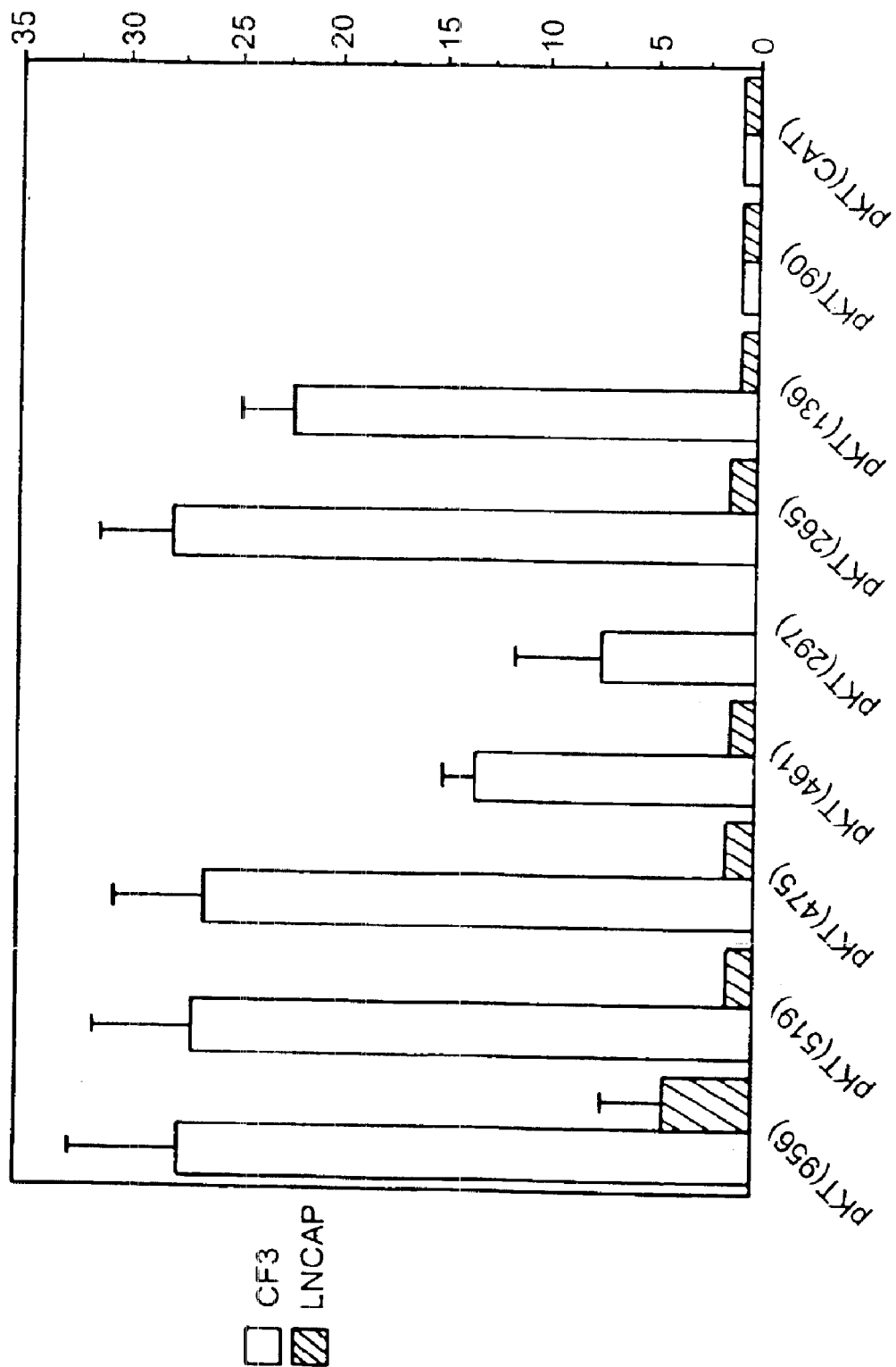
FIG. 9B is a graph depicting the results of CAT assays of various deletion constructs. The CAT constructs were transfected into CF3 and LNCAP cells. Extracts were assayed for CAT activity, and relative activity was determined by normalizing to pKTCAT.

To examine the mechanism of maspin regulation in normal and tumor prostate cells, we prepared a variety of maspin promoter-CAT constructs FIG. 9A. We introduced these constructs into CF3 normal prostate cells and LNCaP prostate tumor cells and measured CAT activity. The results of these experiments are shown in FIG. 9B in which CAT activity is expressed relative to a control construct, pKTCAT, which lacks maspin promoter sequences. In normal CF3 cells, deletion from −956 bp to −475 bp did not alter activity. However, deletion from −475 bp to −461 bp, which removes a distal Ets site, decreased CAT activity about 50%. This indicates the distal Ets site is involved in upregulation of maspin in normal prostate CF3 cells. Further deletion up to −297 bp continued to decrease the activity to about 20% of that observed with an intact maspin promoter, indicating the presence of other unidentified positive cis elements in this region. Deletion from −297 bp to −265 bp removed the HRE element and completely restored the CAT activity in CF3 cells. This result indicates that HRE plays a negative role in transcription. Deletion from −136 bp to −90 bp, which removed a proximal Ets site, completely abolished the CAT activity in CF3 cells.

These data demonstrate that the proximal Ets site is the major positive cis element within 1 kb responsible for upregulation of maspin in normal mammary epithelial cells.

In prostate carcinoma LNCaP cells, the full length promoter (pKT(956)) had very little activity. Deletion from −956 bp to −519 bp decreased the activity further to the level of negative control vector, indicating the presence of a weak positive activation site located within the region. Further deletions gave no CAT activity significantly higher than that of negative control vector, owing that the Ets site is not active in LNCaP tumor cells.

To confirm the involvement of the Ets site in transcriptional activation of maspin, we investigated the ability of Ets to enhance transcription by cloning the Ets site (−120 bp to −90 bp) into the pBLCAT2 vector, which contains no enhancer but a minimal strength tk promoter. This construct was transfected into CF3 and LNCaP cells. These experiments revealed that the presence of the proximal Ets site (single copy) increased the CAT activity of pBLCAT2 in CF3 cells approximately 2.5-fold. No enhancing function was observed in LNCaP cells.

Comparison of Maspin Promoter in Normal Prostate and Mammary Epithelial Cells

Figure 10:
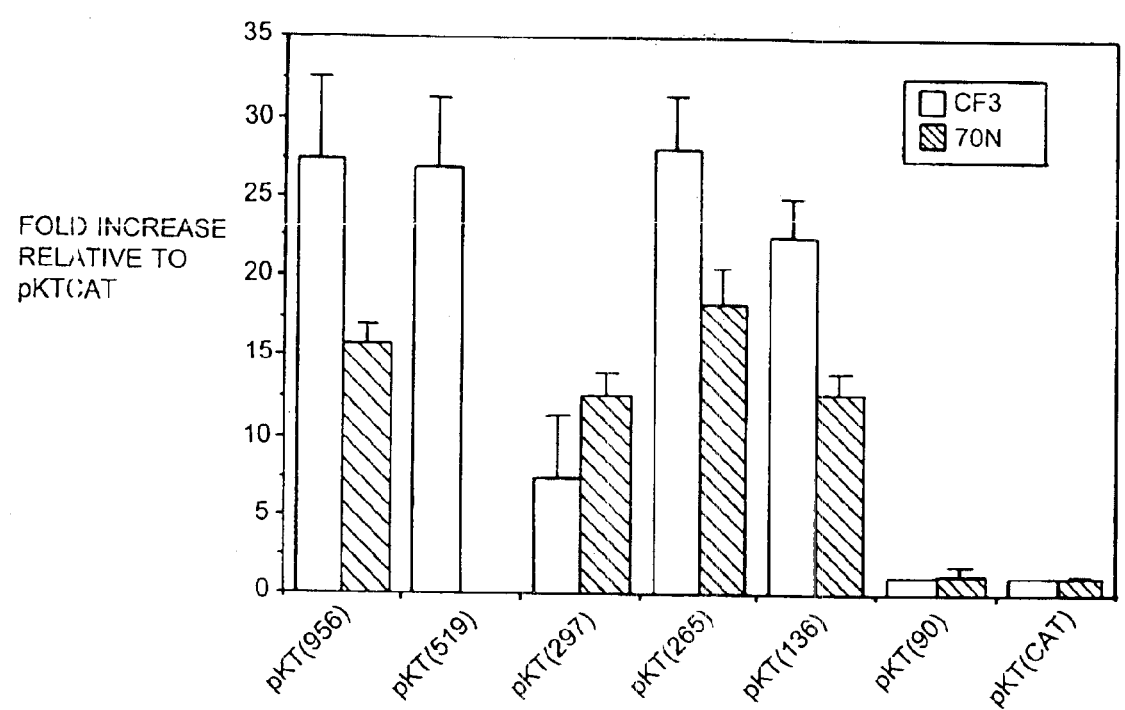
FIG. 10 is a graph depicting the results of CAT assays of various deletion constructs. The CAT constructs were transfected into CF3 and 70N cells. Extracts were assayed for CAT activity, and relative activity was determined by normalizing to pKTCAT.

Activities of the two cis elements in maspin promoter were compared in normal prostate and mammary epithelial cells. The proximal Ets site was identified in both cells as the dominant positive cis element, while the HRE element plays a negative role in transcription in prostate CF3 cells, and is not active in 70N cells (FIG. 10). The distal Ets site seems to play a positive role in transcription in prostate, its effect are balanced by the negative HRE as judged by the fact that deletion of both distal Ets and the HRE sites (pKT (265)) restored activity to the level of full length promoter (pKT (956)).

HRE Site is an Unique Negative Hormonal Response Element in the Maspin Promoter

Figure 11:
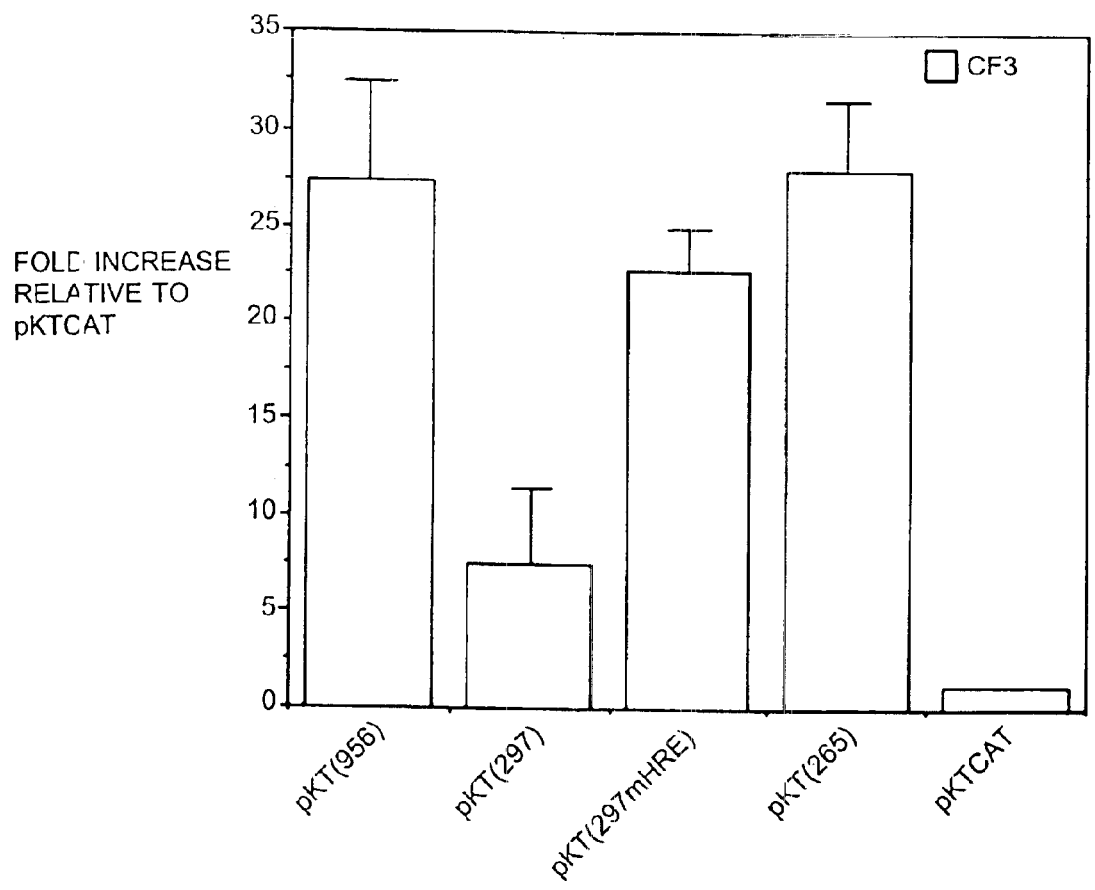
FIG. 11 is a graph depicting the results of CAT assays of various constructs in CF3 cells. Extracts were assayed for CAT activity, and relative activity was determined by normalizing to pKTCAT.

The HRE element has the consensus sequence 5′-GGTACANNNTGT(T/C)CT-3′ (SEQ ID NO: 19) (Beato, Cell 56:335, 1989). This sequence can be recognized by multiple steroid receptors, such as glucocorticoid receptor, androgen receptor, and progesterone receptor. The HRE site (5′ -GTACTCTGATCTCC-3′; SEQ ID NO: 20) in the maspin promoter is unusual in that its sequence is not close to the consensus sequence. To further confirm the activity of this HRE in maspin promoter, we made a mutation in the HRE of pKT(−297) and transfected the mutant construct into the CF3 cells (FIG. 11). Mutation at the HRE site alone specifically blocked the effect of transcription repression, confirming observation from the deletion analysis that the HRE site is a negative hormonal response element.

To test whether the maspin HRE element plays a general role as transcription repressor, we introduced the maspin HRE element upstream of a heterologous promoter, pBLAp1 (pBLCAT2 vector containing the Ap1 enhancer). This construct was used to transfect CF3 cells.

As shown in FIG. 12, pBLAp1 was active in both CF3 and LNCaP cells. The presence of HRE element effectively inhibited promoter activity. Little difference in inhibition was observed between R1881 treated or non-treated samples, indicating the repression mediated by HRE was ligand independent. The extent of repression was similar in both CF3 cells and LNCaP cells, demonstrating the repression mechanism was intact in LNCaP tumor cells as in normal prostate CF3 cells. Accordingly, it appears that active repression through the HRE element contributed to down-regulation of maspin expression in tumor cells.

The Androaen Receptor Binds to the HRE Site of Maspin Promoter

To confirm the presence of steroid receptor binding, oligonucleotides corresponding to the HRE region were end-labeled and used in electrophoresis mobility shift assays with nuclear extracts from CF3 normal epithelial cells, and LNCaP tumor cells. A specific DNA-protein complex was identified with both CF3 and LNCaP nuclear extracts. The complex could be competed by cold HRE oligonucleotides but not by non-specific oligonucleotides (NS). Interestingly, it was not competed by a consensus HRE, indicating high affinity for maspin HRE element.

To test the hypothesis that androgen receptor binds to the HRE site, monoclonal antibody against androgen receptor was added in the reaction mixture. Anti-androgen receptor antibody completely blocked the formation of androgen receptor-DNA complex rat IgG and anti-glucocorticoid receptor antibody did not block complex formation.

These results indicate that androgen receptor, but not glucocorticoid receptor, binds to the HRE site of maspin promoter. We have identified a negative HRE site using promoter analysis and gel shifting experiments and shown that transcription of maspin is repressed by HRE. Interestingly, this repression is androgen-independent in both CF3 normal prostate cells and LNCaP tumor cells.

Maspin may serve as a prognostic marker for prostate cancer. Our data show that maspin is expressed in normal prostate cells and down-regulated in prostate tumor cells. Comparison of maspin promoter regulation in the prostate and mammary gland demonstrates that the regulation of maspin, at least at the transcriptional level, is similar in both organs. It is reasonable to speculate that maspin expression may decrease with increasing malignancy of primary prostate tumors. Recently, we have found that maspin is present in normal prostatic cells but not in tumor cells, using in situ hybridization techniques. Together, these data pose maspin as a potential marker and a promising target for therapeutic intervention in prostate cancer.

Prostate tumors are extremely heterogenic tumors with subpopulations exhibiting different levels of invasiveness in the same organ. From the therapeutic point of view, re-expression of maspin in the prostate tumors offers great hope for reversing the tumor phenotypes. Re-expression may be achieved by targeting both activation and repression modes. For primary tumors, it is likely that the activation is partially impaired, but the repression function in intact. Thus, it may be possible to block the repression mediated by the binding HRE element. Ligands that block the binding of androgen receptor to the maspin HRE can be used to reduce HRE-mediated repression of maspin expression. This may reduce the progressiveness of prostate cancer.

Because the level of maspin expression decreases as malignancy increases, prostate cancer may be staged by measuring the level of maspin expression. Maspin expression can be measured at the MRNA or protein (e.g., by Western blot) level. The level of maspin in a patient is tissue sample is compared to the level in a normal (non-cancerous) control tissue sample or a tissue sample taken from the patient at an earlier time.

What is claimed is:

1. An isolated nucleic acid molecule comprising the nucleotide sequence of nucleotides 451–914 of SEQ ID NO:1.

2. The isolated nucleic acid molecule of claim 1, comprising the nucleotide sequence of nucleotides 451–957 of SEQ ID NO:1.

3. The isolated nucleic acid molecule of claim 1, comprising the nucleotide sequence of nucleotides 1–1141 of SEQ ID NO:1.

4. A nucleic acid vector comprising the isolated nucleic acid molecule of any of claims 1, 2 and 3.

5. The vector of claim 4 further comprising a reporter gene operably linked to the isolated nucleic acid molecule.

6. The vector of claim 5, wherein the reporter gene is selected from the group consisting of β lactamase, chloramphenicol acetyltransferase (CAT), adenosine deaminase (ADA), aminoglycoside phosphotransferase (ncor, G418r), dihydrofolate reductase (DHFR), hygromycin B phosphotransferase (HPH), thymidine kinase (TK), lacZ (encoding β galactosidase), and xanthine guanine phosphoribosyltransferase (XGPRT).

7. The vector of claim 6, wherein the vector is a plasmid.

8. The vector of claim 6, wherein the vector is a virus.

9. The vector of claim 8, wherein the virus is a retrovirus.

10. An isolated host cell comprising the vector of claim 4.

11. An isolated host cell comprising the vector of claim 5.

* * * * *

SEQUENCE LISTING

<160> NUMBER OF SEQ ID NOS: 20

<210> SEQ ID NO 1
<211> LENGTH: 1141
<212> TYPE: DNA
<213> ORGANISM: Homo sapiens

<400> SEQUENCE: 1

```
agataagcac agcagagaag caaccagctc cgtttcaggt cctttcctga ggctgattcg      60
gctggaaggg agtaggtccc accaaatgaa gaagctgtgg gaagacagga ggacaagaac     120
aggctccacg aagagatttc agagcagagc tgcgtactcc ttttctttt tgtttctttt      180
gctctgtcac ccaggctgaa gtacagtggt tagctcacgg ctcactgcag ctttgacctc     240
ccaggctcaa gtgatcctct cgtctcagct ttccaagtaa ctgggaccac aggcatgcat     300
caccacgcta ggctattgtt ttacatttt tgtagagatg gggtctcacc atgttgccca      360
ggttggtctc aaactcctgg gctcaagcaa tccgctcacg tcaacctccc caaatgctgg     420
gattacaggc gtgagccacc gggccaggc tgagtaatcc taatcacagg attttaaaaa      480
gaaacttcct gcgccaccca ttaaacaata tctcctacca atttggtagt aaatatttg      540
ctaatagtac ctaatttta gtaggcact gtgtttatac atatatccat tccttctttt       600
ttgattgtct ttctgtttaa tgggcagcta cctctcttgg catctagcag aatgagctgc     660
tgcagtttac acaaaaagaa tggagatcag agtactttt gtgccaccaa cgtgtctgag      720
aaatttgtag tgttactatc atcacacatt acttttattt catcgaatat ttcaccttcc     780
ggtcctgcgt gggccgagag gattgccgta cgcatgtctg tacgtatgca tgtaactcac     840
agccccttcc tgcccgaaca tgttggaggc cttttggaag ctgtgcagac aacagcaact     900
tcagcctgaa tcatctcttt caattgtgga caagctgcca agaggcttga gtaggagagg     960
agtgccgccg aggcggggcg gggcggggcg tggagctggg ctggcagtgg gcgtggcggt    1020
gctgccagg tgagccaccg ctgcttctgc ccagacacgg tcgcctccac atccaggtct    1080
ttgtgctcct cgcttgcctg ttccttttcc acgcattttc caggataact gtgactccag    1140
g                                                                   1141
```

<210> SEQ ID NO 2
<211> LENGTH: 51
<212> TYPE: DNA
<213> ORGANISM: Artificial Sequence
<220> FEATURE:
<223> OTHER INFORMATION: oligonucleotide for PCR

<400> SEQUENCE: 2

```
tcaccagtta tcctggaaaa tgcgtggaaa aggaacaggc aagcgaggag c               51
```

<210> SEQ ID NO 3
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 3

```
cagccccttc ctgcccgaac                                                  20
```

<210> SEQ ID NO 4
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 4
gtcggggaag gacggggctt g                                              21

<210> SEQ ID NO 5
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 5
cagccccttt ttgcccgaac                                                20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 6
gtcggggaaa aacgggcttg                                                20

<210> SEQ ID NO 7
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 7
ccttgtcaga caggcaagtg cc                                             22

<210> SEQ ID NO 8
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 8
ggaacagtct gtccgttcac gg                                             22

<210> SEQ ID NO 9
<211> LENGTH: 19
<212> TYPE: DNA
<213> ORGANISM: Artificial Sequence
<220> FEATURE:
<223> OTHER INFORMATION: oligonucleotide for PCR

<400> SEQUENCE: 9
agtactctga tctccattc                                                 19

<210> SEQ ID NO 10
<211> LENGTH: 19
<212> TYPE: DNA
<213> ORGANISM: Artificial Sequence
<220> FEATURE:
<223> OTHER INFORMATION: oligonucleotide for PCR

<400> SEQUENCE: 10
gaatggagat cagagtact                                                      19

<210> SEQ ID NO 11
<211> LENGTH: 27
<212> TYPE: DNA
<213> ORGANISM: Artificial Sequence
<220> FEATURE:
<223> OTHER INFORMATION: oligonucleotide for PCR

<400> SEQUENCE: 11
ctaggctgta caggatgttc tgcctag                                             27

<210> SEQ ID NO 12
<211> LENGTH: 27
<212> TYPE: DNA
<213> ORGANISM: Artificial Sequence
<220> FEATURE:
<223> OTHER INFORMATION: oligonucleotide for PCR

<400> SEQUENCE: 12
gatccgacat gtcctacaag acggatc                                             27

<210> SEQ ID NO 13
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 13
ccttgtcaga caggcaagtc c                                                   21

<210> SEQ ID NO 14
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 14
ggaacagtct grccgttcac gg                                                  22

<210> SEQ ID NO 15
<211> LENGTH: 38
<212> TYPE: DNA
<213> ORGANISM: Artificial Sequence
<220> FEATURE:
<223> OTHER INFORMATION: oligonucleotide for PCR

<400> SEQUENCE: 15
aactgcagtt tacacaaaaa gaatgatatc cggagtac                                 38

<210> SEQ ID NO 16
<211> LENGTH: 28
<212> TYPE: DNA
<213> ORGANISM: Artificial Sequence
<220> FEATURE:
<223> OTHER INFORMATION: oligonucleotide for PCR

<400> SEQUENCE: 16
ggtggtatat ccagtgattt ttttctcc                                            28

```
<210> SEQ ID NO 17
<211> LENGTH: 25
<212> TYPE: DNA
<213> ORGANISM: Artificial Sequence
<220> FEATURE:
<223> OTHER INFORMATION: oligonucleotide for PCR

<400> SEQUENCE: 17
gatccagtac tctgatctcc attcg                                          25

<210> SEQ ID NO 18
<211> LENGTH: 25
<212> TYPE: DNA
<213> ORGANISM: Artificial Sequence
<220> FEATURE:
<223> OTHER INFORMATION: oligonucleotide for PCR

<400> SEQUENCE: 18
gatccgaatg gagatcagag tactg                                          25

<210> SEQ ID NO 19
<211> LENGTH: 15
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: (1)...(15)
<223> OTHER INFORMATION: n = A,T,C or G

<400> SEQUENCE: 19
ggtacannnt gtyct                                                     15

<210> SEQ ID NO 20
<211> LENGTH: 14
<212> TYPE: DNA
<213> ORGANISM: Homo sapiens

<400> SEQUENCE: 20
gtactctgat ctcc                                                      14
```